United States Patent [19]
Löhn

[11] Patent Number: 5,961,327
[45] Date of Patent: Oct. 5, 1999

[54] DENTAL TREATMENT DEVICE

[75] Inventor: Gerd Löhn, Biberach-Rissegg, Germany

[73] Assignee: Kaltenbach & Voigt GmbH & Co., Biberach-Rissegg, Germany

[21] Appl. No.: 09/035,318

[22] Filed: Mar. 5, 1998

[30] Foreign Application Priority Data

Mar. 7, 1997 [DE] Germany .......................... 197 09 499

[51] Int. Cl.⁶ .................................................. A61C 17/00
[52] U.S. Cl. ................................ 433/80; 433/29; 433/126
[58] Field of Search ................................ 433/80, 82, 84, 433/29, 126, 146, 88, 85, 32

[56] References Cited

U.S. PATENT DOCUMENTS

| | | | |
|---|---|---|---|
| 4,249,899 | 2/1981 | Davis | 433/80 |
| 4,398,885 | 8/1983 | Loge et al. | 433/29 |
| 4,479,499 | 10/1984 | Alfano . | |
| 4,521,189 | 6/1985 | Lares et al. | 433/84 |
| 4,592,728 | 6/1986 | Davis | 433/80 |
| 4,753,595 | 6/1988 | Schuss et al. | 433/29 |
| 4,902,225 | 2/1990 | Lohn | 433/80 |
| 5,057,015 | 10/1991 | Fleer | 433/29 |
| 5,431,566 | 7/1995 | Blair et al. | 433/126 |
| 5,538,425 | 7/1996 | Reeves et al. | 433/82 |
| 5,833,684 | 11/1998 | Franetzki | 606/17 |

FOREIGN PATENT DOCUMENTS

| | | |
|---|---|---|
| 33 39 650 A1 | 5/1985 | Germany . |
| 35 30 461 A1 | 3/1987 | Germany . |
| 42 00 741 A1 | 7/1993 | Germany . |
| 93 17 984 | 5/1995 | Germany . |

*Primary Examiner*—Gene Mancene
*Assistant Examiner*—Pedro Philogene
*Attorney, Agent, or Firm*—Scully, Scott, Murphy & Presser

[57] ABSTRACT

The invention relates to a dental treatment instrument with which a dental handpiece (1), at its instrument end and/or at its hose end, is provided with unlocking planes (4a, 4b) which cooperate with correspondingly complementarily formed unlocking planes (5a, 5b) of a dental treatment instrument (2) or of a hose connection (3) of a supply hose. The treatment instrument (2) or the supply hose (3) can, because of the cooperating unlocking planes (4a, 4b; 5a, 5b), be released by simple turning of the treatment instrument (2) or of the supply hose (3) relative to the dental treatment instrument.

23 Claims, 4 Drawing Sheets

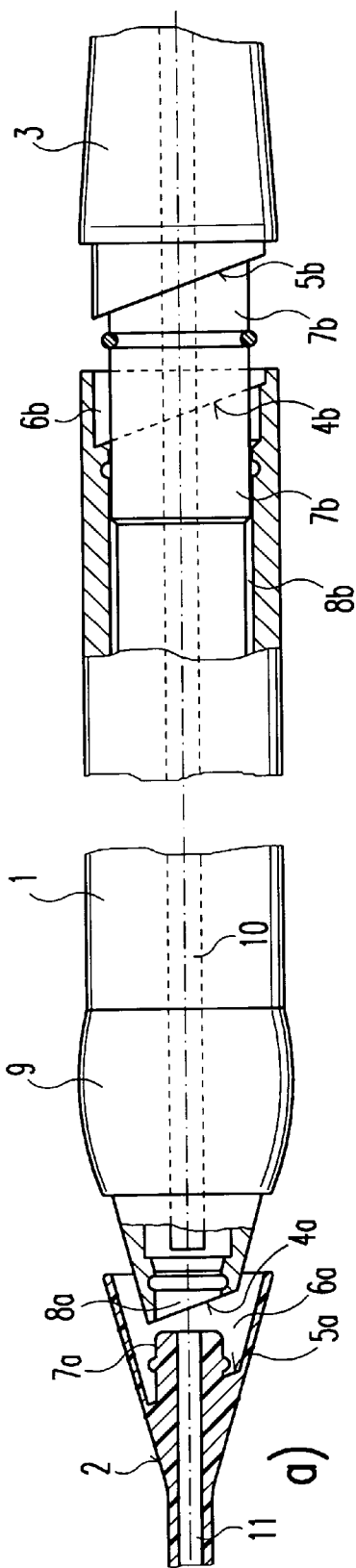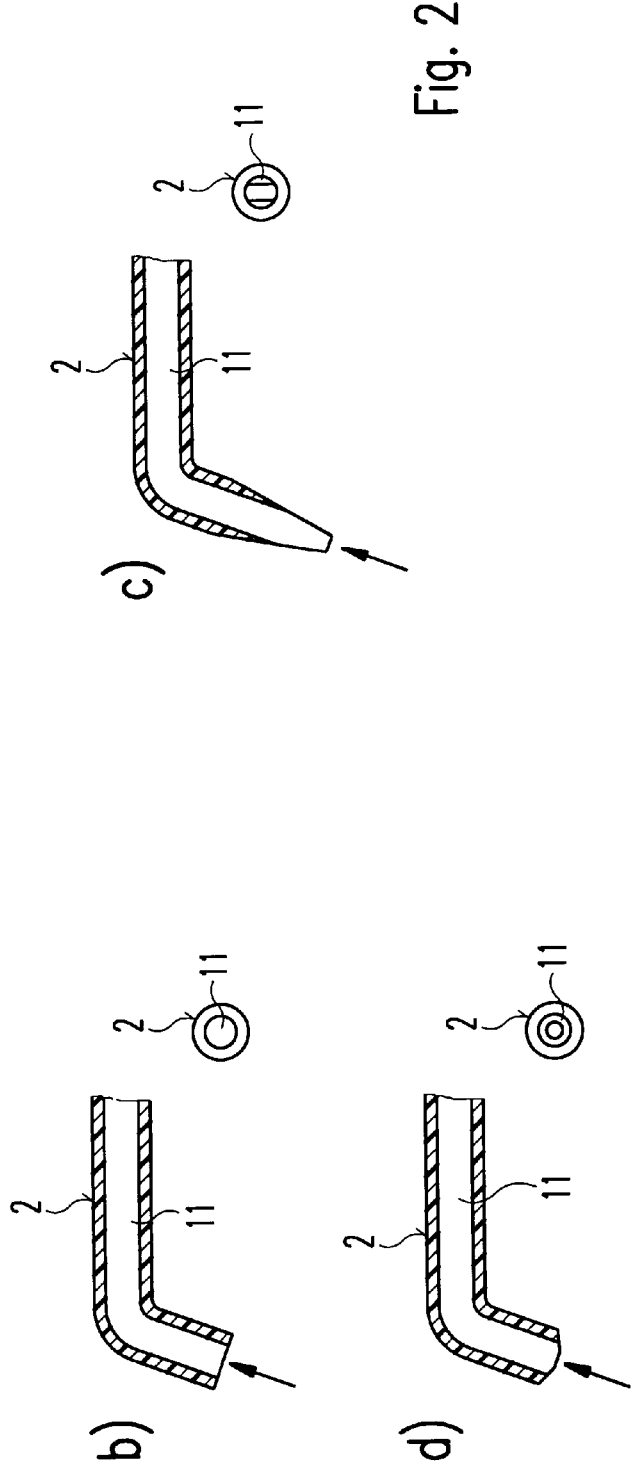
Fig. 2

DENTAL TREATMENT DEVICE

BACKGROUND OF THE INVENTION

1. Field of the Invention

The present invention relates to a dental treatment device, in particular a dental treatment device for the recognition of caries, plaque or bacterial infection of teeth.

2. Discussion of the Prior Art

Dental treatment devices include, as is known, a dental handpiece to which, on the one hand, a dental treatment instrument or tool can be applied and, on the other hand, to which a supply hose can be connected which in turn is connected with a control device which delivers to the handpiece having the dental treatment instrument, via the supply hose, the respective appropriate operating medium for the dental treatment instrument, such as e.g. current, cooling water, cooling spray or light. In the case of a dental treatment device for the recognition of caries, plaque or bacterial infection of teeth, the dental treatment instrument is a light probe, which irradiates the tooth to be investigated with primary light radiation and at the same time detects, as secondary light radiation, fluorescence radiation excited at the irradiated tooth, and delivers the secondary light radiation to the control device. The control device determines, on the basis of the spectral properties of the detected secondary radiation, the carious condition of the investigated tooth. Corresponding devices are described for example in U.S. Pat. No. 4,479,499, DE-A1-42 00 741 or DE-U1-93 17 984.

With the known dental treatment devices, the dental treatment instrument is either screwed on to the dental handpiece or plugged on to the dental handpiece. In the case of screwing on, for removal of the dental treatment instrument it is necessary to screw it off of the dental handpiece. In the case of plugging on, the dental treatment instrument is fixed on the dental handpiece by means of a press fit, so that for the removal and withdrawing of the dental treatment instrument a relatively large application of force is necessary. As a rule, the supply hose is also screwed on to or plugged on to the handpiece, so that with regard to the coupling between the supply hose of the dental handpiece the above-said likewise applies.

SUMMARY OF THE INVENTION

The object of the present invention is thus to provide a dental treatment device with which the taking off or removal of the dental treatment instrument and of the supply hose from the dental handpiece is facilitated.

In accordance with the present invention, the parts of the dental treatment device to be connected are equipped in each case with complementary releasing slants or releasing planes which run obliquely to the longitudinal direction of the dental handpiece, so that for the release of the plugged-together parts merely a rotation of the coupled-together parts, relative to one another in the circumferential direction of the dental handpiece is necessary. In that in the plugged-together condition the release planes of the coupled parts abut one another, the coupled parts are automatically distanced from one another, in the longitudinal direction of the dental handpiece, by means of the turning of the dental handpiece in the circumferential direction, so that for releasing the connection a pulling in the longitudinal direction of the dental handpiece is no longer necessary. In this way, the force necessary to release the coupled parts is significantly reduced.

BRIEF DESCRIPTION OF THE DRAWINGS

The invention will be described in more detail below with reference to preferred exemplary embodiments and with reference to the accompanying drawings, which show.

DETAILED DESCRIPTION OF PREFERRED EMBODIMENTS

The dental treatment device in accordance with the invention will be described below with reference, by way of example, to a dental treatment device for the detection of caries, plaque or bacterial infection of teeth. Of course, the invention can however also be applied to other dental treatment devices with which, instead of a light probe, other treatment instruments or treatment tools, such as e.g. drills, spray attachments or other lighting devices can be placed on the dental handpiece.

Figure 1:
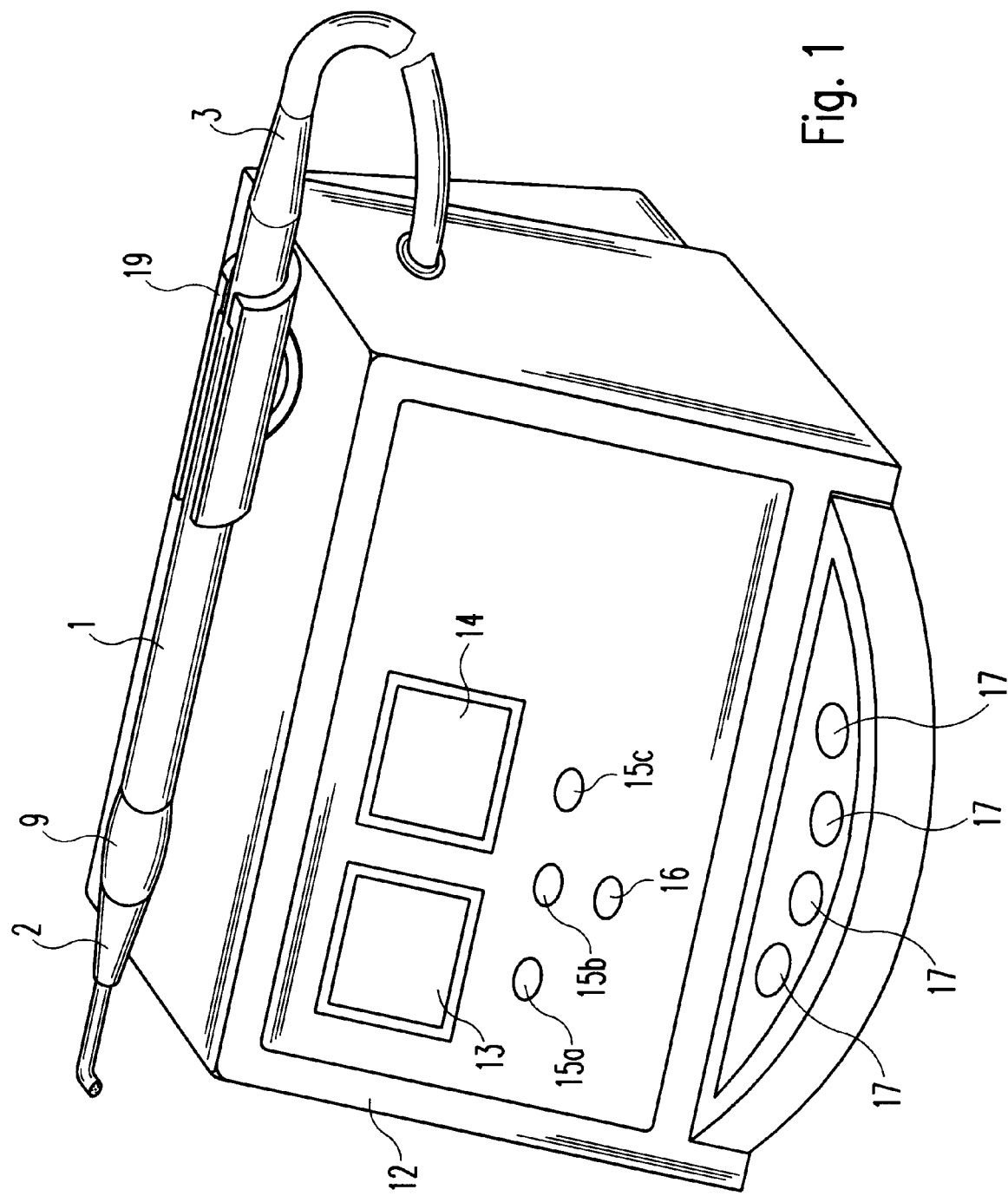
FIG. 1 a dental treatment instrument in accordance with the invention, for the recognition of caries, plaque or bacterial infection of teeth, FIG. 2a an illustration to an enlarged scale of the coupling region between a dental treatment instrument or a supply hose and a dental handpiece with the dental treatment instrument illustrated in FIG. 1, FIG. 2b–d various tip shapes for the light probe illustrated in FIG. 2a, FIG. 3 an illustration to an enlarged scale of the dental handpiece in accordance with the invention, FIG. 4a a view to an enlarged scale of a light probe in accordance with the invention for investigation of smooth tooth surfaces, FIG. 4b a view to an enlarged scale of a light probe in accordance with the invention for the investigation of regions between the teeth (approximal regions), and FIG. 4c an illustration to an enlarged scale of a light probe in accordance with the invention for the investigation of fissures.

FIG. 1 shows an overall illustration of a dental treatment device in accordance with the invention for the detection of caries, plaque or bacterial infection. The treatment device illustrated in FIG. 1 includes a control device 12, a dental handpiece 1 connected with the control device via a supply hose 3, and a dental treatment instrument connected with the dental handpiece 1, in this case a light probe 2. The light probe 2 and/or the hose connection of the supply hose 3 are plugged on to the dental handpiece 1. With the aid of the dental treatment device illustrated in FIG. 1, a tooth to be investigated is irradiated with light, whereby the primary radiation emitted from the light probe 2 excites a fluorescence radiation at the tooth to be investigated. The fluorescence spectrum returned from the tooth thereby manifests significant differences between a healthy (tooth) tissue and a tissue altered (unhealthy) in comparison to the healthy condition. In particular, significant differences appear between carious and healthy tooth regions. The fluorescence spectrum is detected by the light probe 2 and passed on by a light conductor in the dental handpiece 1 and the supply hose 3 to the control device 12 where on the basis of the detected fluorescence radiation intensity a healthy tooth region can be unambiguously distinguished from a carious tooth region. The apparatus shown in FIG. 1 has a display 13 for the display of the actual measurement value of the fluorescence radiation excited at the irradiated tooth and a display 14 for the display of a maximum measurement value (peak value) of the detected fluorescence radiation. As will be explained in more detail, it is proposed in accordance with the invention to employ for different applications or different tooth regions to be investigated, differently formed light probes. For this reason, probe displays 15a–c are provided which by lighting up each indicate the selected light probe 2 plugged on to the dental handpiece.

Advantageously, the treatment device shown in FIG. 1 is operated with a battery or an accumulator as voltage source, so that the treatment device is mobile and light. A warning lamp 16 indicates by lighting up that the voltage delivered from the battery or the accumulator has fallen below a predetermined minimum voltage value and thus must be exchanged or charged. Further, setting keys 17 are provided with the aid of which inter alia a selected and plugged-in light probe 2 can be calibrated and the type of the light probe 2 can be indicated to the control device 12. The dental handpiece 1 can, for example for transportation, be placed in a holder 19. Advantageously the dental handpiece 1 has at its instrument end a ring switch 9. This ring switch is a switch which extends around the dental handpiece 1 in a ring shape and responds to pressure so that via the switch the treatment device can be switched on/off or a particular operating mode can be selected independently of the disposition of the dental handpiece 1 in the hand of the operating person.

FIG. 2a shows an enlarged illustration of the coupling mechanism in accordance with the invention between the dental treatment instrument 2 or supply hose 3 illustrated in FIG. 1 and the dental handpiece 1. The dental handpiece 1 in accordance with the invention has at its instrument end and/or hose end an unlocking plane or unlocking slant 4a or 4b running obliquely to the longitudinal direction of the dental handpiece 1. This unlocking slant 4a or 4b is complementary to an unlocking plane or unlocking slant 5a or 5b of the dental treatment instrument (light probe) 2 or of the hose connection of the supply hose 3 shown in FIG. 1, which unlocking plane or unlocking slant 5a or 5b likewise runs obliquely to the longitudinal direction. The light probe 2 has a hollow space 6a in the contact region which is formed correspondingly to the external shape of the dental handpiece 1 in the contact region, so that by means of plugging the light probe 2 on to the dental handpiece 1 the instrument-end region of the dental handpiece 1 abuts in a fitting manner within the hollow space 6a of the light probe 2. In particular, the unlocking slants 4a and 5a contact one another. The light radiation necessary for the investigation of a tooth is supplied via the supply hose 3 and an internal light conductor of the light probe 2 located in the dental handpiece 1. In order to connect a light conductor 11 present in the light probe 2 with the light conductor 10 arranged in the dental handpiece 1, the light probe 2 has a connection region 7a which projects from the unlocking plane 5a of the light probe 2 into the interior of the hollow space 6a. Upon plugging together of the light probe 2 and the dental handpiece 1, the connection region 7a is received by a receiving opening 8a formed in the obliquely running unlocking plane 4a, so that by means of plugging together of the two parts the light conductors 11 and 10 are connected with one another.

The function of the coupling mechanism in accordance with the invention is now as follows. After assembling together the light probe 2 and the dental handpiece 1 the instrument-end coupling region of the dental handpiece 1 lies in a fitted manner in the hollow space 6a of the light probe 2a. In particular the two unlocking planes 4a and 5a contact one another. Since both the light probe 2 and also the dental handpiece have a circular cross-section in the coupling or contact region, the light probe 2 can be turned with respect to the dental handpiece 1, in the circumferential direction of the dental handpiece 1. Because of the obliquely running unlocking planes 4a and 5a which bear against one another, through turning of the light probe 2 in the circumferential direction of the dental handpiece, the light probe 2 is however inevitably displaced in the longitudinal direction of the dental handpiece 1, i.e. the two parts 1, 2 are automatically separated by turning relative to one another. Since, thus, in accordance with the invention, for the separation of the light probe 2 from the dental handpiece 1, no pulling of the light probe 2 in the longitudinal direction of the dental handpiece 1 away from the handpiece 1 is now necessary, by means of the unlocking mechanism in accordance with the invention the force needed for separating the two parts is significantly reduced.

As with the coupling or unlocking mechanism between the light probe 2 and the dental handpiece 1, the dental handpiece 1 also has at its hose-end an unlocking slant 4b which is formed to be complementary to an unlocking slant 5b formed on the hose connection 3. In the present case, the hose-end unlocking slant 4b of the dental handpiece 1 is arranged in a hollow space 6b of the dental handpiece 1 and has in particular a receiving opening 8b into which a connection region 7b of the hose connection 3 can be introduced. After introduction of this connection region 7b of the hose connection 3 into the hollow space 6b of the dental handpiece, not only the connection region 7b of the supply hose 3 bears in a fitted fashion in the receiving opening 8b of the dental handpiece 1, but the two unlocking planes 5b and 4b contact each other in particular after plugging together of the hose connection 3 and the dental handpiece 1. Since in the coupling region between the dental handpiece 1 and the supply hose 3 both parts have a circular cross-section, the hose connection 3 can again be turned relative to the dental handpiece 3. As already described with reference to the coupling mechanism between the light probe 2 and the dental handpiece 1, by turning relative to the dental handpiece 1, in the circumferential direction of the handpiece, the hose connection 3 is automatically moved away from the dental handpiece 1 in the longitudinal direction of the dental handpiece 1 due to the unlocking slants 4b and 5b bearing against one another, so that a separation of the two parts is possible already by means of turning of the two parts relative to one another, without the hose connection 3 having to be pulled off of the dental handpiece 1 in the longitudinal direction thereof. The necessary application of force for separation of the hose connection 3 from the dental handpiece 1 is thus significantly reduced.

Of course, the arrangement illustrated in FIG. 2a can be modified to the effect that the light probe 2 is received in a hollow space of the dental handpiece 1 or the dental handpiece 1 is received in a hollow space of the hose connection 3, whereby in each case after plugging together of the light probe 2 of the hose connection 3 and the dental handpiece 1, the unlocking planes 4a or 4b and 5a or 5b must contact one another.

Figure 3:
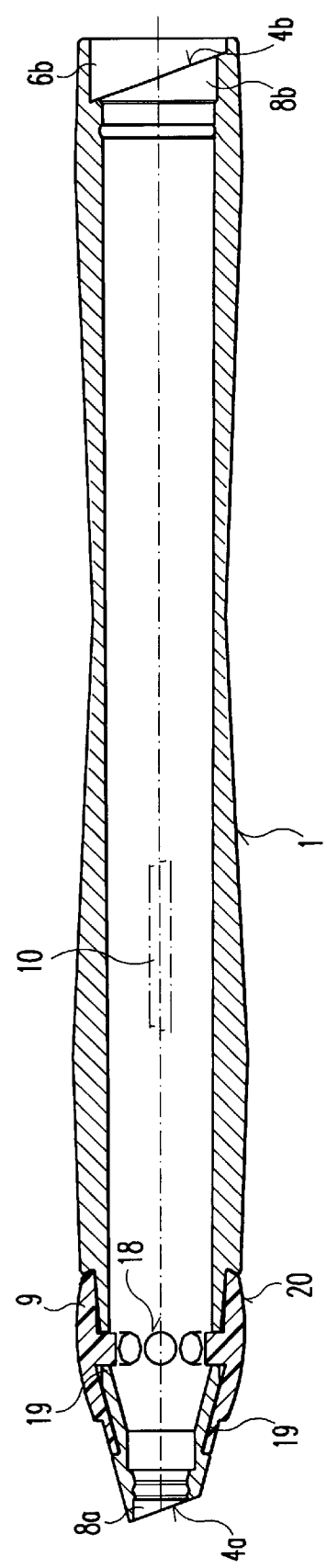

FIG. 3 shows in an illustration to an enlarged scale of the dental handpiece illustrated in FIG. 2a, in cross-section. In particular, in FIG. 3 the two unlocking planes 4a and 4b of the dental handpiece 1 and the two receiving openings 8a and 8b for receiving the projecting connection regions 7a and 7b of the light probe 2 or of the hose connection 3 are illustrated. Likewise in FIG. 3, the ring switch 9 is illustrated in more detail, which ring switch includes an actuating element 20 arranged around the dental handpiece 1 in a ring shape, which with applied force activates contact means 18. The actuating element 20 is elastically pretensioned by means of a spring 19, likewise ring-shaped, arranged around the dental handpiece 1.

As already described with reference to FIG. 1, in accordance with the invention it is proposed that for the detection of caries, plaque or bacterial infection, different light probes are to be employed in dependence upon the configuration of the tooth surface to be investigated. In particular it is proposed to employ three different light probes for the investigation of smooth tooth surfaces, tooth intermediate spaces (approximal regions) or fissures. FIGS. 2b–d show in each case the tip of the corresponding light probe for the investigation of smooth tooth surfaces (FIG. 2b), tooth intermediate spaces (FIG. 2c) and fissures (FIG. 2d) and a view on to the corresponding light probe tip in the arrowed direction. As can be seen from FIGS. 2b–d, the tip of the light probe for the investigation of smooth tooth surfaces develops in a plane manner, whilst the light probe for the investigation of tooth intermediate spaces is pointed and the light probe for the investigation of fissures develops in a rounded manner or is of truncated cone type.

Figure 4:
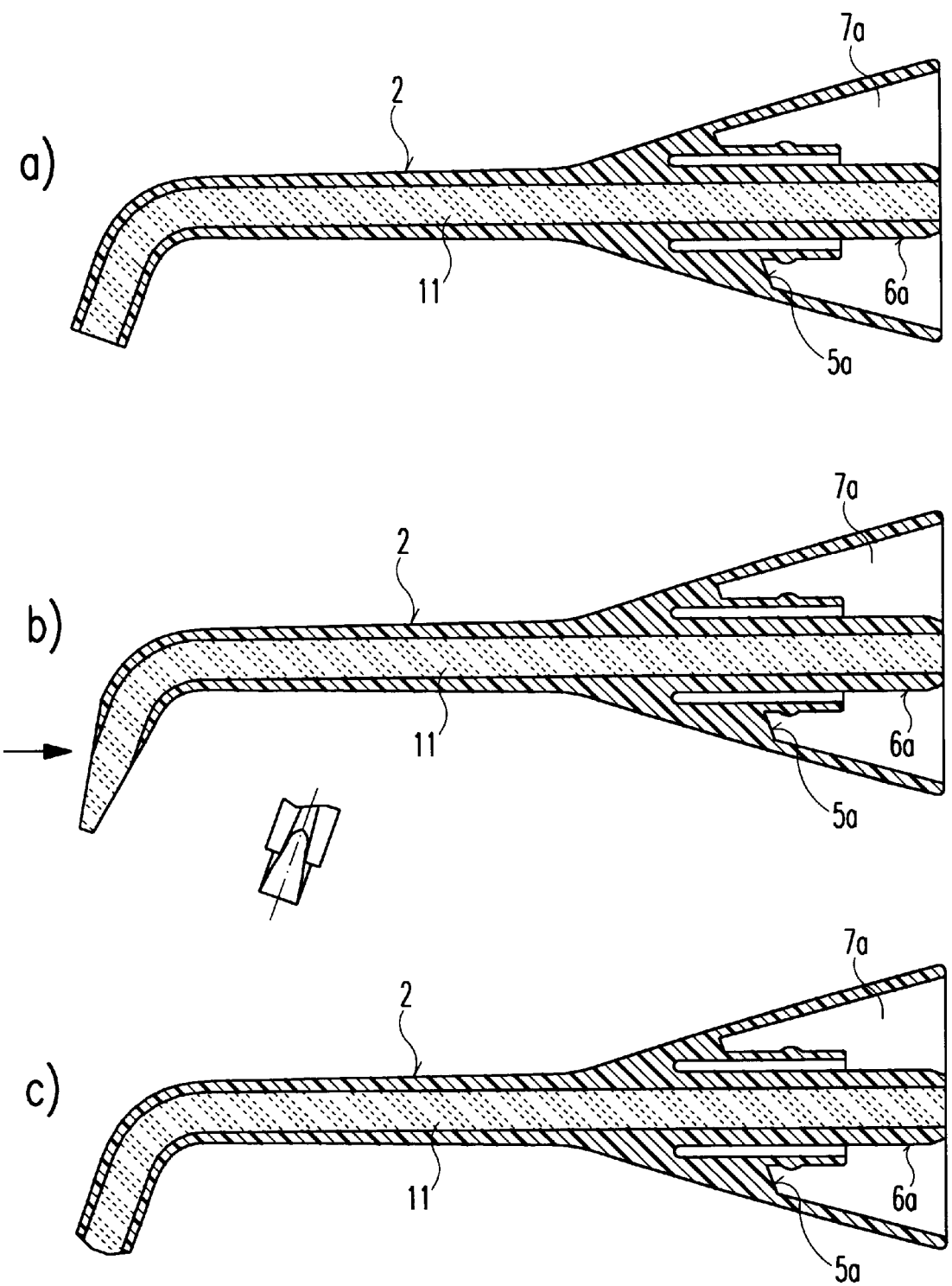

FIGS. 4a–c show a complete view of the light probes corresponding to the light probe tips illustrated in FIGS. 2b–d, whereby in particular the unlocking plane 5a, the hollow space 7a for receiving the instrument-end of the dental handpiece and the projecting connection region 6a, which is introduced into a receiving opening of the dental handpiece, are clearly illustrated. FIG. 4b additionally shows a side view taken in the arrow direction of FIG. 4b, onto the tip for the investigation of tooth intermediate spaces illustrated in FIG. 4b.

I claim:

1. Dental handpiece (1), which at one end thereof can be coupled with a dental treatment instrument (2) and at an opposite end thereof can be connected to a supply hose (3) for the delivery of at least one operating medium serving for the operation of the dental treatment instrument, characterized in that, the dental handpiece (1) has an unlocking plane (4a) at its instrument connecting end and an unlocking plane (4b) at its hose connecting end each running obliquely to the longitudinal direction of the dental handpiece, each of which plane is respectively formed complementary to an obliquely running unlocking plane (5a, 5b) of the dental treatment instrument (2) and of a hose connection of the supply hose (3).

2. Dental treatment instrument (2), which can be plugged on to a dental handpiece (1), characterized in that, the dental treatment instrument (2) has at its handpiece end an unlocking plane (5a) which runs obliquely to the longitudinal direction of the dental treatment instrument, and which is formed complementary to an obliquely running unlocking plane (4a) of the dental handpiece (1).

3. Supply hose (3), which on the one hand can be plugged on to a dental handpiece (1) and on the other hand can be connected to a control device (12) for controlling the delivery of operating medium via the supply hose to the dental handpiece, characterized in that, a handpiece end hose connection of the supply hose (3) has an unlocking plane (5b) which runs obliquely to the longitudinal direction of the hose connection and which is formed complementary to an obliquely running unlocking plane (4b) of the dental handpiece (1).

4. Dental treatment device, having a dental handpiece (1) according to claim 1, having a dental treatment instrument (2), which can be plugged on to an end of the dental handpiece, according to claim 2, having a supply hose (3) that can be plugged on to the other end of the dental handpiece, in order to deliver to the dental handpiece the operating medium necessary for the operation of the dental treatment instrument, and having a control device (12) connected with the supply hose, in order to control the delivery of the suitable operating medium in dependence upon the selected dental treatment instrument.

5. Dental treatment device according to claim 4, characterized in that, in the plugged-on condition, the dental treatment instrument (2) and the supply hose (3) are each firmly coupled with the dental handpiece (1) by means of a press fit, and in that the dental treatment instrument (2) and the supply hose (3) can be unlocked from the dental handpiece (1) solely by turning thereof, relative to the dental handpiece (1), in the circumferential direction of the dental handpiece (1).

6. Dental treatment device according to claim 4, characterized in that, the dental handpiece (1) has at its instrument end an external form which is constituted complementary to a hollow space (6a) of the dental treatment instrument (2), so that in the plugged-together condition the instrument end of the dental handpiece bears in a fitted manner internally in the hollow space of the dental treatment instrument and in particular the unlocking planes (4a, 5a) of the treatment instrument and of the handpiece abut one another.

7. Dental treatment device according to claim 4, characterized in that, the dental handpiece (1) has at least one internal channel (10) in order to deliver to the dental treatment instrument (2) the operating medium delivered from the supply hose (3).

8. Dental treatment device according to claim 7, characterized in that, the dental treatment instrument (2) has a connection region (7a) for receiving the operating medium delivered from the dental handpiece (1), whereby in the plugged-together condition the connection region of the treatment instrument and the internal channel (10) of the handpiece are connected with one another.

9. Dental treatment device according to claim 6, characterized in that, the connection region (7a) of the dental treatment instrument (2) projects into the interior of the hollow space (6a) of the treatment instrument and in the plugged-together condition is received by a receiving opening (8a) of the dental handpiece (1).

10. Dental treatment device according to claim 9, characterized in that, the receiving opening (8a) of the dental handpiece (1) is formed in the unlocking plane (4a) of the handpiece and the connection region (7a) of the dental treatment instrument (2) projects from the unlocking plane (5a) of the treatment instrument.

11. Dental treatment device according to claim 4, characterized in that, the dental treatment instrument (2) has at its handpiece end an exterior form which is constituted complementary to a hollow space of the dental handpiece (1), so that in the plugged-together condition the handpiece end of the dental treatment instrument bears in a fitted manner internally in the hollow space of the dental handpiece and in particular the unlocking planes (4a, 5a) of the dental handpiece and of the treatment instrument butt against one another.

12. Dental treatment device according to claim 4, characterized in that, the hose connection of the supply hose (3) has at its handpiece end an exterior form which is constituted complementary to a hollow space (6b) of the dental handpiece (1), so that in the plugged-together condition the handpiece end of the hose connection bears in a fitted manner internally in the hollow space (6b) of the dental handpiece (1) and in particular the unlocking planes (4b, 5b) of the dental handpiece and of the hose connection butt against one another.

13. Dental treatment device according to claim 12, characterized in that, the hose connection (3) has a connection region (7b) projecting from the unlocking plane (5b) of the hose connection, which connection region is, in the plugged together condition, received by a receiving opening (8b) of the hollow space (6b), formed in the unlocking plane (4b) of the dental handpiece (1).

14. Dental treatment device according to claim 4, characterized in that, the dental handpiece (1) has at its hose end an exterior form which is constituted complementary to a hollow space of the hose connection of the supply hose (3), so that in the plugged together condition the hose end of the dental handpiece (1) bears in a fitted manner in the hollow space of the hose connection and in particular the unlocking planes (4b, 5b) of the dental handpiece and of the hose connection butt against one another.

15. Dental treatment device according to claim 4, characterized in that, the dental treatment instrument (2) is a removable light probe, which in the plugged-together condition is connected with the control device (12) via light conductors (10), and in that the dental treatment device serves for the detection of caries, plaque or bacterial infection of teeth, whereby the light probe (2) irradiates the teeth with primary light radiation and detects secondary fluorescence radiation thus excited at the irradiated teeth, and the control device receives and evaluates the secondary fluorescence radiation via the light conductor (10).

16. Dental treatment device according to claim 15, characterized in that, the dental handpiece (1) can be connected to a plurality of different light probes (2) in dependence upon the intended use.

17. Dental treatment device according to claim 16, characterized in that, there is provided a light probe for the investigation of smooth tooth surfaces, a light probe for the investigation of regions between the teeth, and a light probe for the investigation of fissures.

18. Dental treatment device according to claim 17, characterized in that, the light probe (2) for the investigation of smooth tooth surfaces is flat at its end towards the teeth.

19. Dental treatment device according to claim 17, characterized in that, the light probe (2) for the investigation of regions between the teeth is pointed at its end towards the teeth.

20. Dental treatment device according to claim 17, characterized in that, the light probe (2) for the investigation of fissures is rounded at its end towards the teeth.

21. Dental treatment device according to claim 16, characterized in that, a display (15a–c) is provided for indicating the light probe (2) plugged on to the dental handpiece (1).

22. Dental treatment device according to claim 16, characterized in that, means (17) are provided in order to indicate to the control device (12) the type of light probe (2) plugged on to the dental handpiece (1).

23. Dental treatment device according to claim 17, characterized in that, the light probe (2) for the investigation of for the investigation of fissures is truncated cone shape at its end towards the teeth.

* * * * *